(12) United States Patent
Yao et al.

(10) Patent No.: US 11,612,565 B2
(45) Date of Patent: Mar. 28, 2023

(54) AEROSOLIZABLE GEL

(71) Applicant: NICOVENTURES TRADING LIMITED, London (GB)

(72) Inventors: John Yao, Cambridge, MA (US); Joseph McLellan, Cambridge, MA (US); Xinhua Li, Cambridge, MA (US); Hootan Farhat, Cambridge, MA (US); Michael Bates, Cambridge, MA (US)

(73) Assignee: Nicoventures Trading Limited, London (GB)

( * ) Notice: Subject to any disclaimer, the term of this patent is extended or adjusted under 35 U.S.C. 154(b) by 305 days.

(21) Appl. No.: 16/760,363

(22) PCT Filed: Oct. 31, 2018

(86) PCT No.: PCT/GB2018/053140
§ 371 (c)(1),
(2) Date: Apr. 29, 2020

(87) PCT Pub. No.: WO2019/086860
PCT Pub. Date: May 9, 2019

(65) Prior Publication Data
US 2021/0177039 A1     Jun. 17, 2021

(30) Foreign Application Priority Data

Nov. 1, 2017 (GB) ...................... 1718032

(51) Int. Cl.
*A24B 15/167* (2020.01)
*A61K 9/00* (2006.01)
(Continued)

(52) U.S. Cl.
CPC ............ *A61K 9/007* (2013.01); *A24B 15/167* (2016.11); *A24F 40/20* (2020.01); *A24F 40/10* (2020.01)

(58) Field of Classification Search
CPC ........ A61K 9/007; A24B 15/167; A24F 40/20
See application file for complete search history.

(56) References Cited

U.S. PATENT DOCUMENTS 10,595,558 B2 *   3/2020   Malgat ................. A24D 1/02
2012/0067361 A1   3/2012   Björkholm et al.
(Continued)

FOREIGN PATENT DOCUMENTS

CN     101347477 A     1/2009
CN     101979011 A     2/2011
(Continued)

OTHER PUBLICATIONS

International Preliminary Report of Patentability, International Patent Application No. PCT/GB2018/053140, dated Oct. 7, 2019, 13 pages.
(Continued)

*Primary Examiner* — Tho D Ta
(74) *Attorney, Agent, or Firm* — Patterson Thuente, P.A.

(57) ABSTRACT

There is provided an aerosolizable gel comprising (a) an active agent; (b) one or more gel forming materials, wherein the one or more gel forming material is at least one phyllosilicate; (c) an aerosol forming material selected from glycerol, propylene glycol and mixtures thereof; and (d) water.

19 Claims, 4 Drawing Sheets

(51) Int. Cl.
*A24F 40/20* (2020.01)
*A24F 40/10* (2020.01)

(56) References Cited

U.S. PATENT DOCUMENTS

| | | |
|---|---|---|
| 2015/0209530 A1 | 7/2015 | White |
| 2017/0020183 A1 | 1/2017 | Björkholm |
| 2017/0112183 A1 | 4/2017 | Björkholm |
| 2017/0266087 A1 | 9/2017 | Bouarfa et al. |
| 2018/0279666 A1 | 10/2018 | Aoun et al. |
| 2019/0358332 A1 | 11/2019 | Björkholm |

FOREIGN PATENT DOCUMENTS

| | | | |
|---|---|---|---|
| CN | 102125028 A | 7/2011 | |
| DE | 19854009 A1 | 5/2000 | |
| EP | 0405190 A2 | 1/1991 | |
| EP | 1151751 A1 | 11/2001 | |
| EP | 1501382 B1 * | 12/2009 | ............. A24B 15/16 |
| JP | S53-109933 A | 9/1978 | |
| JP | 2007308443 A | 11/2007 | |
| WO | WO2012019372 A1 | 2/2012 | |
| WO | WO2013036415 A2 | 3/2013 | |
| WO | WO-2017149288 A1 * | 9/2017 | ........... A24B 15/167 |
| WO | WO2019086859 A1 | 5/2019 | |

OTHER PUBLICATIONS

International Search Report and Written Opinion, International Patent Application No. PCT/GB2018/053140, dated Feb. 6, 2019, 75 pages.
Database WPI Week 197844 Thomson Scientific, London, GB; AN 1978-78926A XP002113399, 2017, 2 pages.

* cited by examiner

AEROSOLIZABLE GEL

CROSS-REFERENCE TO RELATED APPLICATIONS

The present application is a National Phase entry of PCT Application No. PCT/GB2018/053140, filed Oct. 31, 2018, which claims priority from Great Britain Patent Application No. 1718032.4 filed Nov. 1, 2017, each of which is fully incorporated herein by reference.

FIELD OF THE INVENTION

The present disclosure relates to an aerosolizable gel, a dosage form of an aerosolizable product, a method of forming an aerosol and to electronic vapor provision systems such as electronic delivery systems (e.g. e-cigarettes) incorporating said aerosolizable gel.

BACKGROUND TO THE INVENTION

Electronic vapor provision systems such as e-cigarettes generally contain a reservoir of liquid which is to be vaporized, typically containing nicotine. When a user inhales on the device, a heater is activated to vaporize a small amount of liquid, which is therefore inhaled by the user.

The use of e-cigarettes in the UK has grown rapidly, and it has been estimated that there are now over a million people using them in the UK.

Current electronic cigarettes generate an aerosol by vaporizing a consumable e-liquid composed mostly of propylene glycol (PG), glycerol, water, nicotine and flavors. The e-liquid is drawn by a wicking material into a resistive heating coil in which it is heated and evaporated. This straight-forward system suffers from a number of drawbacks such as leaking of the e-liquid though gaskets and the mouthpiece, inefficient heating and an inconsistent aerosol composition.

SUMMARY OF THE INVENTION

In one aspect there is provided an aerosolizable gel comprising
(a) an active agent;
(b) one or more gel forming materials, wherein the one or more gel forming material is at least one phyllosilicate;
(c) an aerosol forming material; and
(d) water.

In one aspect there is provided a dosage form of an aerosolizable product, wherein the dosage form of the aerosolizable gel comprises
(a) an active agent in an amount of 0.5 to 10 mg;
(b) one or more gel forming materials, wherein the one or more gel forming materials is at least phyllosilicate;
(c) an aerosol forming material; and
(d) water.

In one aspect there is provided a method of forming an aerosol, the method comprising the step of heating an aerosolizable gel comprising
(a) an active agent;
(b) a gel forming material, wherein the gel forming material is at least one phyllosilicate;
(c) an aerosol forming material; and
(d) water.

In one aspect there is provided an electronic vapor provision system comprising:

(i) an aerosolizable gel comprising
(a) an active agent;
(b) one or more gel forming materials, wherein the one or more gel forming material is at least one phyllosilicate;
(c) an aerosol forming material; and
(d) water;
(ii) a heater for heating the aerosolizable gel and thereby vaporizing some or all of the aerosolizable gel for inhalation by a user of the electronic vapor provision system.

DETAILED DESCRIPTION

As discussed herein, embodiments of the present invention provides an aerosolizable gel include:

(a) an active agent; (b) one or more gel forming materials, wherein the one or more gel forming material is at least one phyllosilicate; (c) an aerosol forming material; and (d) water.

We have found that we may avoid many of the limitations of the e-liquid of the prior art by using a non-liquid gel-medium. Gel-media will allow greater flexibility in the design of future heating technologies and consumable form factors. We have found that the gel heats and vaporizes efficiently. We have also found that the gel consistently delivers the active agent, such as nicotine, and flavors in the aerosol. In particular, the resulting aerosol does not contain any detectable toxicants or malodor component resulting from the thermal degradation of the gel.

We have identified that via selection of a particular gel forming material, namely phyllosilicate, the problems of the prior art my may be overcome. In particular, we have found that the gel materials containing phyllosilicate exhibit a similar heating profile compared to 'raw' liquid. In contrast many prior art gels require significantly longer heating times to aerosolize the same amount of liquid, indicating significantly inhibited heat transfer in these samples. Furthermore, in contrast to prior art samples, the aerosolizable gel of the present invention containing phyllosilicate achieved close to 100% aerosolization of the liquid contained therein. Yet further, the inorganic gelling material used in the present invention, namely phyllosilicate provides a thermally stable gelling material and therefore avoids the possibility of toxicants or malodorous components being provided to the user through the thermal degradation of the gel.

For ease of reference, these and further aspects of the present invention are now discussed under appropriate section headings. However, the teachings under each section are not necessarily limited to each particular section.

Active Agent

The aerosolizable gel comprises an active agent. By "active agent" it is meant an agent which has a biological effect on a subject when the aerosol is inhaled. The one or more active agents may be selected from nicotine, botanicals, and mixtures thereof. The one or more active agents may be of synthetic or natural origin. The active could be an extract from a botanical, such as from a plant in the tobacco family. An example active is nicotine.

In one aspect, the active agent is at least nicotine. Nicotine may be provided at any suitable amount depending on the desired dosage when inhaled by the user. In one aspect nicotine is present in an amount of no greater than 6 wt % based on the total weight of the aerosolizable gel. In one aspect nicotine is present in an amount of from 0.4 to 6 wt % based on the total weight of the aerosolizable gel. In one aspect nicotine is present in an amount of from 0.8 to 6 wt % based on the total weight of the aerosolizable gel. In one aspect nicotine is present in an amount of from 1 to 6 wt % based on the total weight of the aerosolizable gel. In one aspect nicotine is present in an amount of from 1.8 to 6 wt % based on the total weight of the aerosolizable gel. In one aspect nicotine is present in an amount of from 0.4 to 5 wt % based on the total weight of the aerosolizable gel. In one aspect nicotine is present in an amount of from 0.8 to 5 wt % based on the total weight of the aerosolizable gel. In one aspect nicotine is present in an amount of from 1 to 5 wt % based on the total weight of the aerosolizable gel. In one aspect nicotine is present in an amount of from 1.8 to 5 wt % based on the total weight of the aerosolizable gel. In one aspect nicotine is present in an amount of no greater than 4 wt % based on the total weight of the aerosolizable gel. In one aspect nicotine is present in an amount of from 0.4 to 4 wt % based on the total weight of the aerosolizable gel. In one aspect nicotine is present in an amount of from 0.8 to 4 wt % based on the total weight of the aerosolizable gel. In one aspect nicotine is present in an amount of from 1 to 4 wt % based on the total weight of the aerosolizable gel. In one aspect nicotine is present in an amount of from 1.8 to 4 wt % based on the total weight of the aerosolizable gel. In one aspect nicotine is present in an amount of no greater than 3 wt % based on the total weight of the aerosolizable gel. In one aspect nicotine is present in an amount of from 0.4 to 3 wt % based on the total weight of the aerosolizable gel. In one aspect nicotine is present in an amount of from 0.8 to 3 wt % based on the total weight of the aerosolizable gel. In one aspect nicotine is present in an amount of from 1 to 3 wt % based on the total weight of the aerosolizable gel. In one aspect nicotine is present in an amount of from 1.8 to 3 wt % based on the total weight of the aerosolizable gel. In one aspect nicotine is present in an amount of no greater than 1.9 wt % based on the total weight of the aerosolizable gel. In one aspect nicotine is present in an amount of no greater than 1.8 wt % based on the total weight of the aerosolizable gel. In one aspect nicotine is present in an amount of from 0.4 to 1.9 wt % based on the total weight of the aerosolizable gel. In one aspect nicotine is present in an amount of from 0.4 to 1.8 wt % based on the total weight of the aerosolizable gel. In one aspect nicotine is present in an amount of from 0.5 to 1.9 wt % based on the total weight of the aerosolizable gel. In one aspect nicotine is present in an amount of from 0.5 to 1.8 wt % based on the total weight of the aerosolizable gel In one aspect nicotine is present in an amount of from 0.8 to 1.9 wt % based on the total weight of the aerosolizable gel. In one aspect nicotine is present in an amount of from 0.8 to 1.8 wt % based on the total weight of the aerosolizable gel. In one aspect nicotine is present in an amount of from 1 to 1.9 wt % based on the total weight of the aerosolizable gel. In one aspect nicotine is present in an amount of from 1 to 1.8 wt % based on the total weight of the aerosolizable gel. In one aspect nicotine is present in an amount of less than 1.9 wt % based on the total weight of the aerosolizable gel. In one aspect nicotine is present in an amount of less than 1.8 wt % based on the total weight of the aerosolizable gel. In one aspect nicotine is present in an amount of from 0.4 to less than 1.9 wt % based on the total weight of the aerosolizable gel. In one aspect nicotine is present in an amount of from 0.4 to less than 1.8 wt % based on the total weight of the aerosolizable gel. In one aspect nicotine is present in an amount of from 0.5 to less than 1.9 wt % based on the total weight of the aerosolizable gel. In one aspect nicotine is present in an amount of from 0.5 to less than 1.8 wt % based on the total weight of the aerosolizable gel. In one aspect nicotine is present in an amount of from 0.8 to less than 1.9 wt % based on the total weight of the aerosolizable gel. In one aspect nicotine is present in an amount of from 0.8 to less than 1.8 wt % based on the total weight of the aerosolizable gel. In one aspect nicotine is present in an amount of from 1 to less than 1.9 wt % based on the total weight of the aerosolizable gel. In one aspect nicotine is present in an amount of from 1 to less than 1.8 wt % based on the total weight of the aerosolizable gel. In one aspect nicotine is present in an amount of no greater than 2 wt % based on the total weight of the aerosolizable gel. In one aspect nicotine is present in an amount of no greater than 1.8 wt % based on the total weight of the aerosolizable gel.

In the context of the present disclosure, reference to nicotine includes nicotine in both protonated form and in unprotonated form.

In one aspect the gel comprises nicotine in unprotonated form and nicotine in protonated form. In one aspect the gel comprises nicotine in unprotonated form and nicotine in monoprotonated form. Although it is envisaged that the gel typically comprise nicotine in unprotonated form and nicotine in monoprotonated form, it may be that small amounts of diprotonated nicotine are present. In one aspect the gel comprises nicotine in unprotonated form, nicotine in monoprotonated form and nicotine in diprotonated form. As will be understood by one skilled in the art, the protonated form of nicotine is prepared by reacting unprotonated nicotine with an acid. The acids are one or more suitable acids. In one aspect the acid is an organic acid. In one aspect the acid is a carboxylic acid. The carboxylic acid may be any suitable carboxylic acid. In one aspect the acid is a mono-carboxylic acid. In one aspect the acid is selected from the group consisting of benzoic acid, levulinic acid, acetic acid, lactic acid, formic acid, citric acid, pyruvic acid, succinic acid, tartaric acid, oleic acid, sorbic acid, propionic acid, phenylacetic acid, and mixtures thereof Gel Forming Materials As discussed herein, one embodiment of the present invention provides an aerosolizable gel comprising one or more gel forming materials, wherein the one or more gel forming material is at least one phyllosilicate. As is understood by one skilled in the art, phyllosilicates are silicate minerals formed by parallel sheets of silicate tetrahedra. The silicate tetrahedra are $Si_2O_5$ or are silicate and oxygen in a 2:5 ratio.

In one aspect the phyllosilicate is selected from the group consisting of the phyllosilicates ajoite, allophane, annite, apophyllite, apophyllite-(KF), bentonite, biotite, bowenite, brammallite, carletonite, caryopilite, cavansite, chamosite, chapmanite, chlorite group, chrysocolla, clay, clay minerals, clintonite, cymrite, delessite, dickite, ekanite, ephesite, expanded clay aggregate, fraipontite, franklinphilite, fuchsite, greenalite, gyrolite, halloysite, hisingerite, imogolite, kampfite, kaolinite, kegelite, kerolite, lepidolite, macaulayite, macdonaldite, magadiite, medicinal clay, meerschaum pipe, metal clay, mica, minnesotaite, nelenite, neptunite, okenite, organoclay, pentagonite, phlogopite, pimelite, pyrophyllite, sanbornite, searlesite, sepiolite, seraphinite, sericite, sericitic alteration, siderophyllite, soapstone, stilpnomelane, talc, thuringite, tumchaite, tuperssuatsiaite, ussingite, zakharovite, zussmanite and mixtures thereof.

In one aspect the phyllosilicate is at least kaolinite. As will be understood by one skilled in the art, kaolinite is a clay mineral, part of the group of industrial minerals, with the chemical composition $Al_2Si_2O_5(OH)_4$. It is a layered silicate mineral, with one tetrahedral sheet of silica ($SiO_4$) linked through oxygen atoms to one octahedral sheet of alumina ($AlO_6$) octahedra. Rocks that are rich in kaolinite are known as kaolin or china clay. References herein to kaolin are to be read as references to kaolinite.

The gel forming material and phyllosilicate in particular may be provided at any suitable amount depending on the desired composition of the final gel. In one aspect phyllosilicate is present in an amount of 10 to 90 wt. % based on the total weight of the aerosolizable gel. In one aspect phyllosilicate is present in an amount of 10 to 80 wt. % based on the total weight of the aerosolizable gel. In one aspect phyllosilicate is present in an amount of 20 to 80 wt. % based on the total weight of the aerosolizable gel. In one aspect phyllosilicate is present in an amount of 30 to 80 wt. % based on the total weight of the aerosolizable gel. In one aspect phyllosilicate is present in an amount of 20 to 70 wt. % based on the total weight of the aerosolizable gel. In one aspect phyllosilicate is present in an amount of 30 to 70 wt. % based on the total weight of the aerosolizable gel. In one aspect phyllosilicate is present in an amount of 20 to 60 wt. % based on the total weight of the aerosolizable gel. In one aspect phyllosilicate is present in an amount of 30 to 60 wt. % based on the total weight of the aerosolizable gel. In one aspect phyllosilicate is present in an amount of 40 to 60 wt. % based on the total weight of the aerosolizable gel.

The gel forming material and kaolinite in particular may be provided at any suitable amount depending on the desired composition of the final gel. In one aspect kaolinite is present in an amount of 10 to 90 wt. % based on the total weight of the aerosolizable gel. In one aspect kaolinite is present in an amount of 10 to 80 wt. % based on the total weight of the aerosolizable gel. In one aspect kaolinite is present in an amount of 20 to 80 wt. % based on the total weight of the aerosolizable gel. In one aspect kaolinite is present in an amount of 30 to 80 wt. % based on the total weight of the aerosolizable gel. In one aspect kaolinite is present in an amount of 20 to 70 wt. % based on the total weight of the aerosolizable gel. In one aspect kaolinite is present in an amount of 30 to 70 wt. % based on the total weight of the aerosolizable gel. In one aspect kaolinite is present in an amount of 20 to 60 wt. % based on the total weight of the aerosolizable gel. In one aspect kaolinite is present in an amount of 30 to 60 wt. % based on the total weight of the aerosolizable gel. In one aspect kaolinite is present in an amount of 40 to 60 wt. % based on the total weight of the aerosolizable gel.

As will be appreciated by one skilled in the art, in one aspect the aerosolizable gel may contain other gel forming materials in addition to the phyllosilicate. In one aspect the aerosolizable gel contains no other gel forming materials in addition to the phyllosilicate. Thus in one aspect the aerosolizable gel comprises gel forming materials consisting of phyllosilicate.

In one aspect the one or more gel forming materials is present in an amount of 10 to 90 wt. % based on the total weight of the aerosolizable gel. In one aspect the one or more gel forming materials is present in an amount of 10 to 80 wt. % based on the total weight of the aerosolizable gel. In one aspect the one or more gel forming materials is present in an amount of 20 to 80 wt. % based on the total weight of the aerosolizable gel. In one aspect the one or more gel forming materials is present in an amount of 30 to 80 wt. % based on the total weight of the aerosolizable gel. In one aspect the one or more gel forming materials is present in an amount of 20 to 70 wt. % based on the total weight of the aerosolizable gel. In one aspect the one or more gel forming materials is present in an amount of 30 to 70 wt. % based on the total weight of the aerosolizable gel. In one aspect the one or more gel forming materials is present in an amount of 20 to 60 wt. % based on the total weight of the aerosolizable gel. In one aspect the one or more gel forming materials is present in an amount of 30 to 60 wt. % based on the total weight of the aerosolizable gel. In one aspect the one or more gel forming materials is present in an amount of 40 to 60 wt. % based on the total weight of the aerosolizable gel.

Aerosol Forming Material

The aerosol forming material of the aerosolizable gel is provided such that the aerosolizable gel produces a vapor under the appropriate heating conditions. The aerosol forming material may contain aerosol forming components such as glycerol, propylene glycol and mixtures thereof. In one aspect the aerosol forming material is at least glycerol. In one aspect the aerosol forming material consists essentially of glycerol. In one aspect the aerosol forming material consists of glycerol. In one aspect the aerosol forming material is at least propylene glycol. In one aspect the aerosol forming material consists essentially of propylene glycol. In one aspect the aerosol forming material consists of propylene glycol. In one aspect the aerosol forming material is at least a mixture of propylene glycol and glycerol. In one aspect the aerosol forming material consists essentially of a mixture of propylene glycol and glycerol. In one aspect the aerosol forming material consists of a mixture of propylene glycol and glycerol.

The aerosol forming material of the aerosolizable gel may be present in any suitable amount. In one aspect the aerosol forming material is present in an amount of 1 to 90 wt % based on the aerosolizable gel. In one aspect the aerosol forming material is present in an amount of 5 to 90 wt % based on the aerosolizable gel. In one aspect the aerosol forming material is present in an amount of 10 to 90 wt % based on the aerosolizable gel. In one aspect the aerosol forming material is present in an amount of 10 to 80 wt % based on the aerosolizable gel. In one aspect the aerosol forming material is present in an amount of 10 to 70 wt % based on the aerosolizable gel. In one aspect the aerosol forming material is present in an amount of 10 to 60 wt % based on the aerosolizable gel. In one aspect the aerosol forming material is present in an amount of 20 to 60 wt % based on the aerosolizable gel. In one aspect the aerosol forming material is present in an amount of 10 to 50 wt % based on the aerosolizable gel. In one aspect the aerosol forming material is present in an amount of 20 to 50 wt % based on the aerosolizable gel. In one aspect the aerosol forming material is present in an amount of 10 to 40 wt % based on the aerosolizable gel. In one aspect the aerosol forming material is present in an amount of 20 to 40 wt % based on the aerosolizable gel.

Water

The aerosolizable gel further comprises water. The water may be present in any suitable amount. In one aspect water is present in an amount of 1 to 50 wt % based on the aerosolizable gel. In one aspect water is present in an amount of 5 to 50 wt % based on the aerosolizable gel. In one aspect water is present in an amount of 1 to 45 wt % based on the aerosolizable gel. In one aspect water is present in an amount of 5 to 45 wt % based on the aerosolizable gel. In one aspect water is present in an amount of 1 to 40 wt % based on the aerosolizable gel. In one aspect water is present in an amount of 5 to 40 wt % based on the aerosolizable gel. In one aspect water is present in an amount of 1 to 35 wt % based on the aerosolizable gel. In one aspect water is present in an amount of 5 to 35 wt % based on the aerosolizable gel. In one aspect water is present in an amount of 1 to 30 wt % based on the aerosolizable gel. In one aspect water is present in an amount of 5 to 30 wt % based on the aerosolizable gel. In one aspect water is present in an amount of 1 to 25 wt % based on the aerosolizable gel. In one aspect water is present in an amount of 5 to 25 wt % based on the aerosolizable gel. In one aspect water is present in an amount of 1 to 20 wt % based on the aerosolizable gel. In one aspect water is present in an amount of 5 to 20 wt % based on the aerosolizable gel. In one aspect water is present in an amount of 1 to 15 wt % based on the aerosolizable gel. In one aspect water is present in an amount of 5 to 15 wt % based on the aerosolizable gel.

In one aspect the combined amount of aerosol forming material and water in the aerosolizable gel is from 1 to 90 wt % based on the aerosolizable gel. In one aspect the combined amount of aerosol forming material and water in the aerosolizable gel is 5 to 90 wt % based on the aerosolizable gel. In one aspect the combined amount of aerosol forming material and water in the aerosolizable gel is 1 to 80 wt % based on the aerosolizable gel. In one aspect the combined amount of aerosol forming material and water in the aerosolizable gel is 5 to 80 wt % based on the aerosolizable gel. In one aspect the combined amount of aerosol forming material and water in the aerosolizable gel is 10 to 80 wt % based on the aerosolizable gel. In one aspect the combined amount of aerosol forming material and water in the aerosolizable gel is 10 to 70 wt % based on the aerosolizable gel. In one aspect the combined amount of aerosol forming material and water in the aerosolizable gel is 15 to 70 wt % based on the aerosolizable gel. In one aspect the combined amount of aerosol forming material and water in the aerosolizable gel is 10 to 60 wt % based on the aerosolizable gel. In one aspect the combined amount of aerosol forming material and water in the aerosolizable gel is 15 to 60 wt % based on the aerosolizable gel. In one aspect the combined amount of aerosol forming material and water in the aerosolizable gel is 20 to 60 wt % based on the aerosolizable gel. In one aspect the combined amount of aerosol forming material and water in the aerosolizable gel is 25 to 60 wt % based on the aerosolizable gel. In one aspect the combined amount of aerosol forming material and water in the aerosolizable gel is 20 to 50 wt % based on the aerosolizable gel. In one aspect the combined amount of aerosol forming material and water in the aerosolizable gel is 25 to 50 wt % based on the aerosolizable gel. In one aspect the combined amount of aerosol forming material and water in the aerosolizable gel is 30 to 50 wt % based on the aerosolizable gel.

Further Components

The gel may also comprise flavoring components. As used herein, the terms "flavor" and "flavorant" refer to materials which, where local regulations permit, may be used to create a desired taste or aroma in a product for adult consumers. Thus, whilst it is acknowledged that some other functional components of the formulation may contain components that have a perceptible flavor or aroma, such components are not added for this purpose and as such are not considered to be a "flavor" or "flavorant" in the context of the present invention. Furthermore, it will be understood that "flavors" or "flavorants" may well composed of one or more individual compounds that together form an identifiable flavor. As such, reference here to "flavor" or "flavorant" includes both singular and multi-component flavors. They may include extracts (e.g. licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, pigment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, or powder.

Dosage Form

Figure 1:
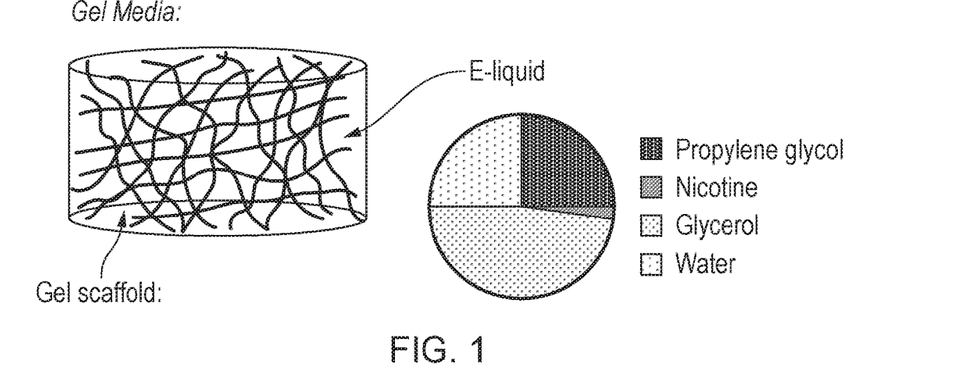

As discussed herein in one aspect, one embodiments of the present invention provides a dosage form of an aerosolizable product, wherein the dosage form of the aerosolizable gel comprises (a) active agent in an amount of 0.5 to 10 mg;

(b) one or more gel forming materials, wherein the one or more gel forming materials is at least phyllosilicate;

(c) an aerosol forming material; and (d) water.

In one aspect, the active agent is nicotine. In one aspect the nicotine is present in an amount of 0.5 to 5 mg. In one aspect the nicotine is present in an amount of 0.5 to 4 mg. In one aspect the nicotine is present in an amount of 0.5 to 3 mg. In one aspect the nicotine is present in an amount of 0.5 to 2 mg. In one aspect the nicotine is present in an amount of 1 to 5 mg. In one aspect the nicotine is present in an amount of 1 to 4 mg. In one aspect the nicotine is present in an amount of 1 to 3 mg. In one aspect the nicotine is present in an amount of 1 to 2 mg.

Method

As discussed herein in one aspect, one embodiment of the present invention provides a method of forming an aerosol, the method comprising the step of heating an aerosolizable gel comprising (a) an active agent;

(b) a gel forming material, wherein the gel forming material is at least one phyllosilicate;

(c) an aerosol forming material; and (d) water.

Electronic Vapor Provision System

The aerosolizable gel may be contained or delivered by any means.

Throughout the following description the term "e-cigarette" is used; however, this term may be used interchangeably with electronic vapor provision system. As discussed herein, the aerosolizable gel of the present invention is typically provided for the delivery of formulation to or within an e-cigarette. The aerosolizable gel may be held within an e-cigarette or may be sold separately, for example as one unit doses, for subsequent use with or in an e-cigarette. In one aspect the aerosolizable gel is contained within an e-cigarette. Therefore in a further aspect the present invention provides an electronic vapor provision system comprising: (i) an aerosolizable gel comprising (a) an active agent; (b) one or more gel forming materials, wherein the one or more gel forming material is at least one phyllosilicate; (c) an aerosol forming material; and (d) water; (ii) a heater for heating the aerosolizable gel and thereby vaporizing some or all of the aerosolizable gel for inhalation by a user of the electronic vapor provision system.

BRIEF DESCRIPTION OF THE DRAWINGS

The present invention will now be described in further detail by way of example only with reference to the accompanying figure in which:

FIG. 1: Gels are composed of gel forming scaffolds holding onto a base e-liquid.

FIG. 4a: Evaporation rate data for various gels. Initial mass loss vs. time collected on a 10 puff equivalent samples on a 250° C. hot plate.

FIG. 4b: Zoom of shaded are from FIG. 4a (first 200 seconds).

FIG. 4c: Time required to evaporate 99% of the e-liquid for various gels. Data collected using the rapid heating apparatus.

FIG. 4d: Current-voltage energy consumed while heating samples from FIG. 4a.

The invention will now be described with reference to the following non-limiting example.

EXAMPLES

Formulations
Base e-liquid:
Propylene glycol 25 wt. %
Water 25 wt. %
Nicotine 1.86 wt. %
Glycerol 48.14 wt. %
Kaolinite—Barrisurf XD available from Imerys For 10 g batch of 60% Kaolinite gel, mix 6 g Kaolinite with 4 g e-liquid The formulations described herein provided a gelled product comprising propylene glycol, nicotine, glycerol and water held together with a gel scaffold in the manner shown in FIG. 1.

Figure 2:
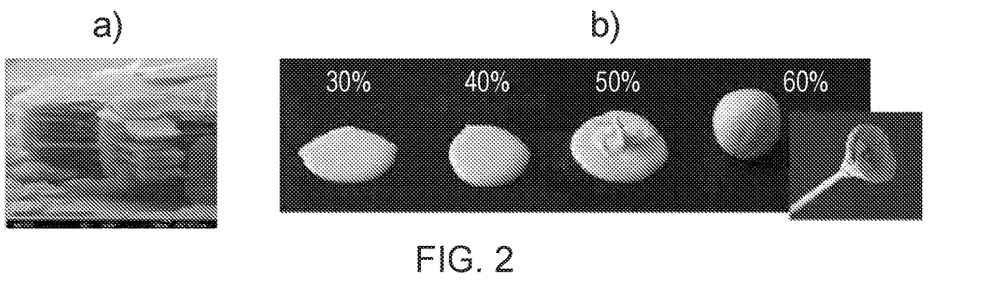
FIG. 2a: SEM micrograph of kaolin clay (Barrisurf XD)
FIG. 2b: Gels made with kaolin clay loading levels between 30% and 60%

Kaolin clay is an aluminosilicate ($Al_2Si_2O_5(OH)_4$) consisting of stacked platelets (FIG. 2a). We used Barrisurf HX, a kaolin supplied as a powder from Imerys with a shape factor of ~100. The kaolin powder was combined as-supplied with the e-liquid and manually stirred until the mixture was homogeneous. FIG. 2b shows the consistency of the mixtures with kaolin loading levels from 30% to 60%. Over this range, the mixture takes on a consistency ranging from thick liquid to a modeling clay-like putty. Like many clay-based pastes, these gels have a shear thinning rheology.

Testing Results:
Energy of Vaporization

Figure 3:
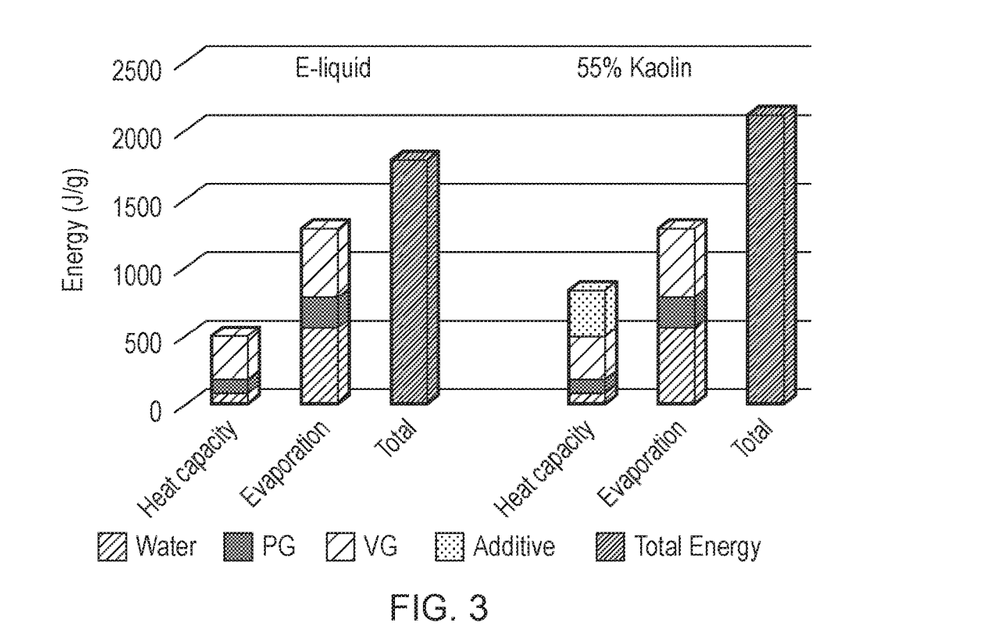
FIG. 3: Calculated energy of vaporization for the e-liquid and 55% kaolin gel. The total energy includes heat capacity contributions from each element of the gel as well as latent heat of evaporation contributions for the e-liquid components.
Figure 4:
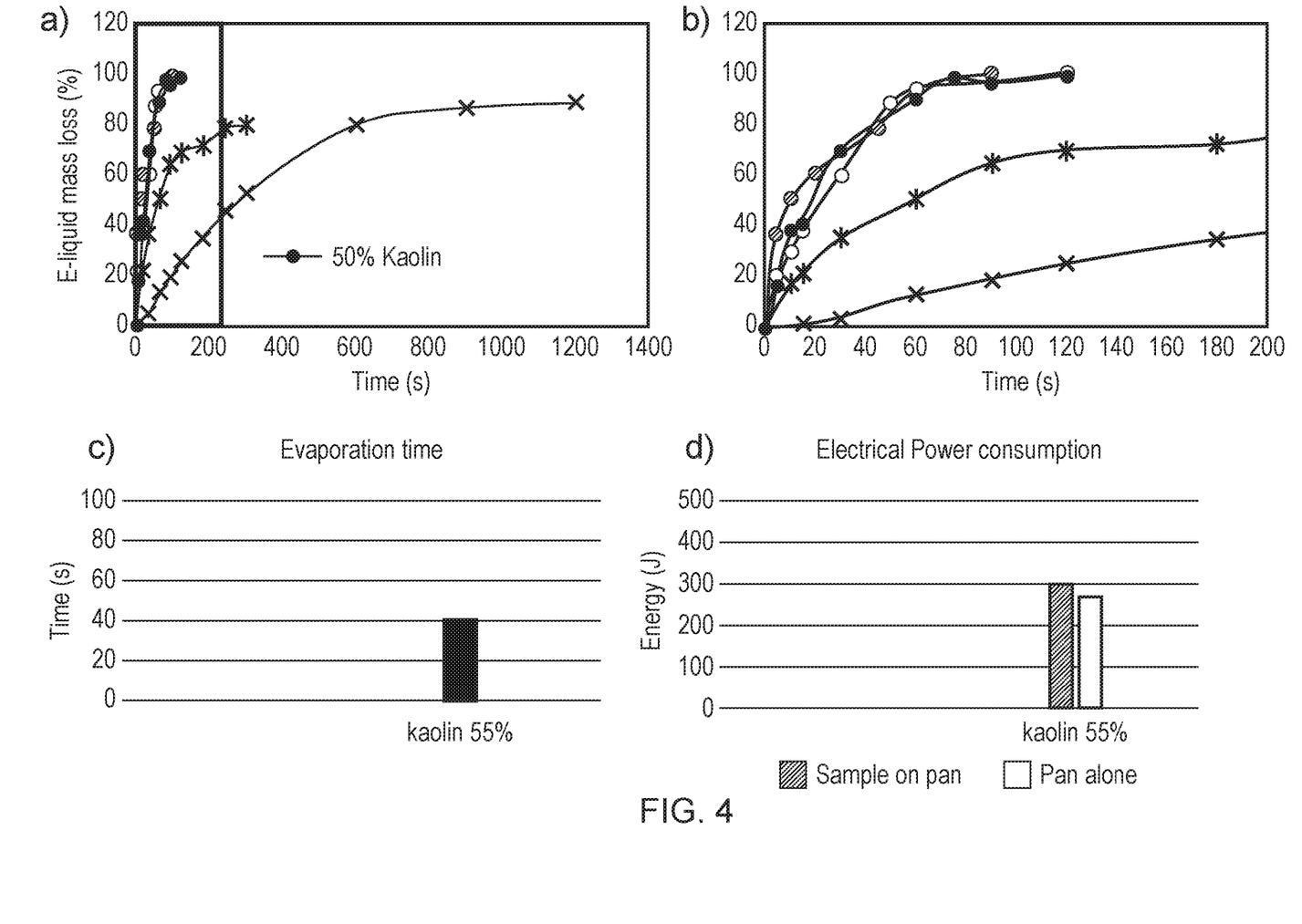
Figure 5:
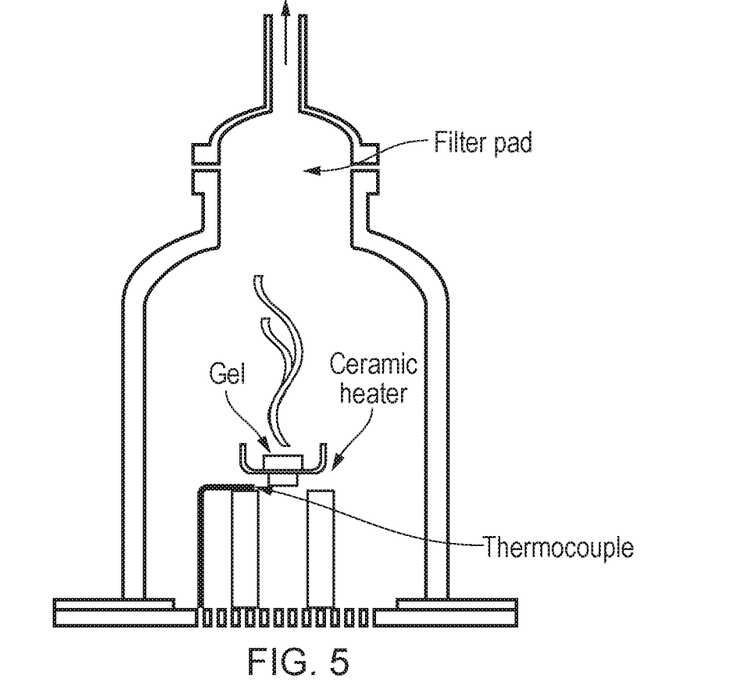
FIG. 5: Aerosol generation/collection apparatus.

For formulations with significant loading levels of additives, the added thermal mass of the additives should be considered. A crude estimate of the energy required to vaporize each formulation can be made by adding up the energy required to heat each component to its boiling point and the latent heat for each component to be vaporized. The contribution from each component is shown in FIG. 3 for the e-liquid as well as kaolin gels Despite only comprising 25% of the formulation, the water accounts for a significant portion of the energy require to vaporize the e-liquid.

Table: Energy required to evaporate various gel from heat flow data obtained using differential scanning calorimetry. The total energy was calculated by integrated the heat flow data from 25° C. to 300° C.

|  | ΔH (kJ/g) |
| --- | --- |
| E-liquid | 1.39 |
| 55% Kaolin | 1.90 |

Experimentally the energy required to vaporize the gels were measured by differential scanning calorimetry. The above Table shows the integrated heat flow in the heating range from 25° C. to 300° C. This measurement confirms that the added contribution to the energy required to vaporize from significant levels of kaolinite is minor.

Evaporation Kinetics:

The evaporation rate of the gels was determined gravimetrically by measuring the mass loss as a function of heating time. Initial measurements were performed by heating gel samples on hot plate—later, this was replaced by faster heating aerosol test rig. Sample sizes were chosen such that samples from the different formulations each contain the same mass of e-liquid (5-10 puff equivalents).

FIG. 4*a* shows the mass loss vs time for kaolinite gel. These measurements were performed on a 10 puff equivalent (containing ~1 mg nicotine) and were heated on a 250° C. hotplate. On this time-scale, the kaolinite gel exhibited similar heating profiles compared to the raw e-liquid.

Aerosol test rig: In order to heat the gels on a time-scale closer to that of an e-cigarette device, we constructed a test rig for rapidly heating the gel and collecting the aerosol (FIG. 5). All subsequent evaporation rate measurements were performed on this device. The heating element (a ceramic disc resistive element) was used to heat samples in a 25 mg aluminum pan. A set-point of 300° C. can be reached within ~3-5 seconds. The heater sits in a glass chamber which is used to collect the aerosol onto a glass filter.

FIG. 4*c* shows the heating time and energy required to aerosolize 55% kaolinite gel. The sample (5 puff equivalent) was heated to 300° C. and held for set durations. The change in sample mass was measured to determine the time required to vaporize 99% of the e-liquid in the sample. In addition to this gravimetric analysis, we also monitored power consumption to vaporize the sample and compared it to the energy required to heat the aluminum pan alone for that duration (FIG. 4*d*).

Aerosol Extraction and GC/MS Analysis:

The composition of the aerosols generated from the five puff gel equivalents were analyzed by gas chromatography-mass spectrometry (GC/MS). The aerosol generated on the heating apparatus was collected onto a glass filter pad by evacuating the chamber with a vacuum pump. Deposits on the filter pad and on the chamber walls were extracted in methanol and analyzed.

The aerosol was collected by placing an inverted Sterlitech glass filtration apparatus (Cat. #311420) over the heater, with a Whatman 47 mm glass microfiber filter pad (Cat. #1821-047) attached to the apparatus to collect the aerosol. The filtration apparatus was connected to an Airpo pump (model #D2028B), with a maximum pump-rate of 12-15 LPM. The pump was set to begin running upon initiation of heating and to continue running for at least 10 seconds after the sample e-liquid was completely aerosolized. The filter was then placed in 10 mL of anhydrous methanol (Sigma-Aldrich Cat. #322415) in a 100 mL glass jar. The aerosol was extracted from the filter pad by gentle shaking of the jar for 30-60 sec. After initial extraction, the filter pad was removed from the methanol extraction solvent, squeezed to remove excess methanol and used to wipe the area around the sample holder pan and the exposed surfaces of the heating rig. The filter was then placed back in the methanol solvent to extract for another 30-60 sec, then removed from methanol, squeezed dry and used to wipe any remaining aerosol residue from the inside of the glass filtration apparatus. The filter pad was then placed back into the methanol solvent for a final 1-2 min of extraction, after which it was removed from the solvent, squeezed dry one final time and discarded. The methanol with the extracted aerosol was transferred into a 1 mL GC/MS vial with a rubber-septum cap and analyzed using an auto-liquid sampler attached to the Agilent 7820A GC with 5977E MSD. The GC/MS procedure used a DB-WAX GC column (30 m length, 0.25 mm diameter, 0.25 μm film thickness, Cat. #122-7032) for analyte separation. The procedure was optimized to resolve the peaks corresponding to: propylene glycol, nicotine and glycerol. The GC procedure is as follows:

| Parameter | Value |
| --- | --- |
| Oven: | |
| Initial Temp. | 50° C. |
| Rate | 30° C./min |
| Final Temp. | 260° C. |
| Final Hold Time | 2 min |
| Inlet: | |
| Temp. | 300° C. |
| Mode | Split |
| Split Ratio | 10:01 |
| Split Flow Rate | 20 mL/min |
| Pressure | 16.9 psi |
| Column: | |
| Model # | 122-7032 |
| Description | DB-WAX |
| Max Temp. | 260° C. |
| Length | 30 m |
| Diameter | 0.25 mm |
| Film Thickness | 0.25 gm |
| Mode | Constant Flow |
| Flow Rate | 2 mL/min |
| Average Velocity | 51.5 cm/sec |

To quantify the relative ratios of the e-liquid components, the peak areas from aerosol extraction results were compared to peak areas of a set of standards. The standards used to produce a calibration curve were made by diluting pure e-liquid in anhydrous methanol. The e-liquid was first diluted 100-fold by pipetting 100 uL of e-liquid into 9.9 mL of anhydrous methanol using micropipettes. The standards were then further diluted and labeled according to their nicotine content. The stock 1:100 dilution contained 1860 ppm nicotine and was used to make standards containing 10, 20, 30, 40 & 50 ppm nicotine. The anhydrous methanol was run as a blank, followed by the calibration curve standards. A fresh set of standards was made and analyzed for each series of extraction samples to ensure accurate calibration.

Figure 6:
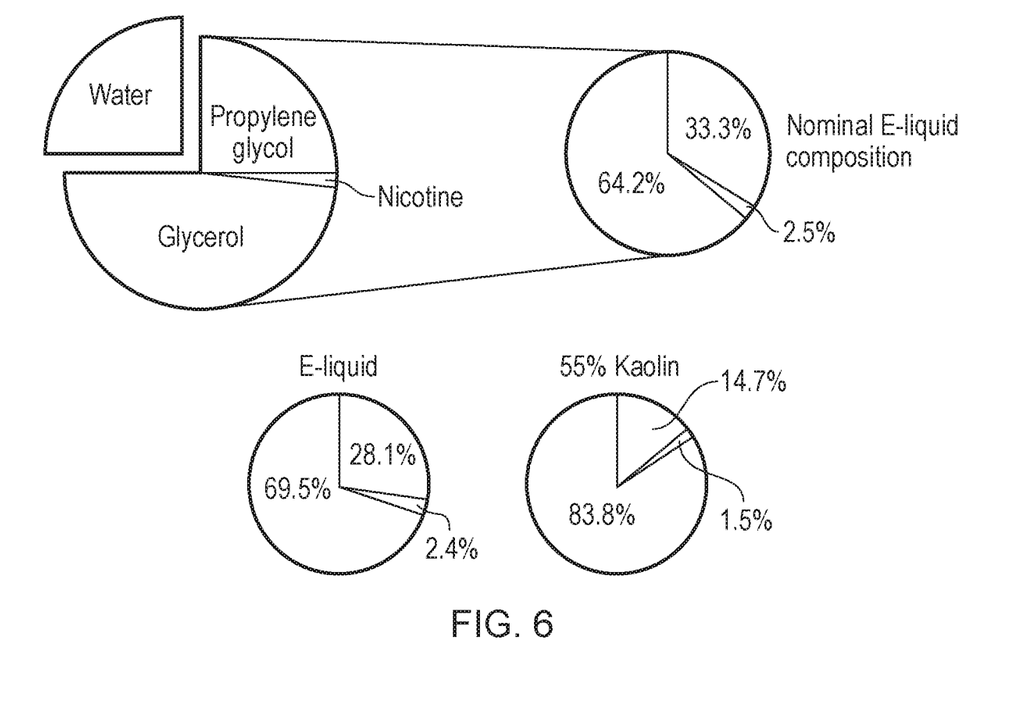
FIG. 6: Aerosol composition.

We found it challenging to quantify the water content of the aerosol due to varying amounts absorbed during the aerosol collection. The water absorption could not be accounted for by running a blank filter through the extraction process. We, therefore, focused on quantifying the relative compositions of the remaining three components of the aerosol. The results are presented in the form of pie-charts in FIG. 6. The composition of the e-liquid was very close to the nominal e-liquid composition. The 55%-Kaolinite gel contains an increased proportion of glycerol. Because these samples required a longer heating time therefore also a longer pumping time, we suspect that the PG and nicotine components may be pulled through the collection pad along with some water content.

Thermal Stability of Additives:

Although the only volatile components of the formulated gels are the e-liquid components, compounds produced by thermal degradation of the gels could contribute volatile toxicants and undesirable flavor to the aerosol. Thermogravimetric analysis was performed on the gel additives to characterize the temperature at which they decomposed and give-off volatile components.

Thermogravimetric analysis on the dry powder gel additives was performed using a Shimadzu TGA-50. Each sample weighed 15-20 mg and were heated in an open aluminum pan (VWR 12577-060). The additives were heated to 600° C. at a rate of 20° C./min in an air atmosphere at a flow rate of 100 mL/min. Combined thermogravimetric analysis and differential scanning calorimetry were performed of fully formulated gels using a TA Instruments Q600. The samples were placed in covered alumina pans and an identical covered alumina pan was used for the DSC reference. Simultaneous TGA and DSC data was collected analyzed by heating to 400° C. at 10° C./min with a gas flow rate of 100 mL/min air.

Figure 7:
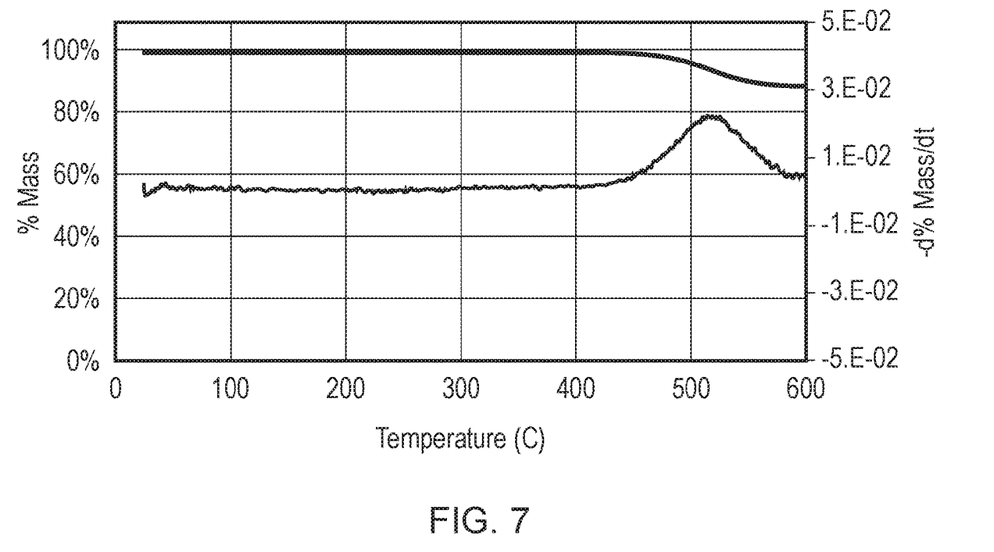
FIG. 7: Thermogravimetric analysis data for kaolinite gel product.

Kaolinite did not show any signs of degradation in the relevant temperature range. Thermogravimetric analysis data for Kaolinite is shown in FIG. 7.

Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention claimed is:

1. A dosage form of an aerosolizable product, wherein the dosage form of the aerosolizable gel comprises:
    (a) nicotine in an amount of 0.5 to 10 mg;
    (b) one or more gel forming materials, wherein the one or more gel forming materials is at least kaolinite;
    (c) an aerosol forming material; and
    (d) water.

2. An aerosolizable gel according to claim 1 wherein the nicotine is present in an amount of no greater than 2 wt % based on the total weight of the aerosolizable gel.

3. An aerosolizable gel according to claim 1 wherein the nicotine is present in an amount of no greater than 1.8 wt % based on the total weight of the aerosolizable gel.

4. An aerosolizable gel according to claim 1 wherein the kaolinite is present in an amount of 10 to 80 wt. % based on the aerosolizable gel.

5. An aerosolizable gel according to claim 1 wherein the kaolinite is present in an amount of 20 to 70 wt. % based on the aerosolizable gel.

6. An aerosolizable gel according to claim 1 wherein the kaolinite is present in an amount of 30 to 60 wt. % based on the aerosolizable gel.

7. An aerosolizable gel according to claim 1 wherein the aerosol forming material is selected from glycerol, propylene glycol and mixtures thereof.

8. An aerosolizable gel according to claim 1 wherein the aerosol forming material is a combination of glycerol and propylene glycol.

9. An aerosolizable gel according to claim 1 wherein the aerosol forming material is present in an amount of 10 to 60 wt. % based on the aerosolizable gel.

10. An aerosolizable gel according to claim 1 wherein the aerosol forming material is present in an amount of 20 to 40 wt. % based on the aerosolizable gel.

11. An aerosolizable gel according to claim 1 wherein the water is present in an amount of 1 to 40 wt. % based on the aerosolizable gel.

12. An aerosolizable gel according to claim 1 wherein the water is present in an amount of 1 to 20 wt. % based on the aerosolizable gel.

13. A method of forming an aerosol, the method comprising the step of heating an aerosolizable gel comprising;
   (a) an active agent;
   (b) a gel forming material, wherein the gel forming material is at least kaolinite;

(c) an aerosol forming material; and (d) water.

14. A method of forming an aerosol according to claim 13 wherein the aerosol forming material is selected from glycerol, propylene glycol and mixtures thereof.

15. A method of forming an aerosol according to claim 13 wherein the aerosolizable gel is an aerosolizable gel comprises:

nicotine in an amount of no greater than 2 wt % based on the total weight of the aerosolizable gel;

kaolinite in an amount of 10 to 80 wt. % based on the aerosolizable gel;

the aerosol forming material is present in an amount of 10 to 60 wt. % based on the aerosolizable gel; and water present in an amount of 1 to 20 wt. % based on the aerosolizable gel.

16. An electronic vapour provision system comprising:

(i) an aerosolizable gel comprising (a) an active agent;

(b) one or more gel forming materials, wherein the one or more gel forming material is at least kaolinite;

(c) an aerosol forming material; and (d) water;

(ii) a heater for heating the aerosolizable gel and thereby vaporising some or all of the aerosolizable gel for inhalation by a user of the electronic vapour provision system.

17. A method of forming an aerosol according to claim 16 wherein the aerosolizable gel is an aerosolizable gel comprising:

nicotine in an amount of no greater than 2 wt % based on the total weight of the aerosolizable gel;

kaolinite in an amount of 10 to 80 wt. % based on the aerosolizable gel;

the aerosol forming material is present in an amount of 10 to 60 wt. % based on the aerosolizable gel; and water present in an amount of 1 to 20 wt. % based on the aerosolizable gel.

18. The method of claim 13, wherein the aerosol forming material is a combination of glycerol and propylene glycol.

19. The method of claim 16, wherein the aerosol forming material is a combination of glycerol and propylene glycol.

* * * * *